United States Patent [19]

Poulain

[11] 3,975,377
[45] Aug. 17, 1976

[54] PROCESS FOR PREPARING N-ALKYL-LACTAMS

[75] Inventor: Claude Poulain, Orsay, France

[73] Assignee: Ato Chimie, Courbevoie, France

[22] Filed: Mar. 28, 1975

[21] Appl. No.: 562,905

[52] U.S. Cl. .................. 260/239.3 R; 260/239.3 A
[51] Int. Cl.² ...................................... C07D 201/14
[58] Field of Search ............ 260/239.3 R, 239.3 A

[56] References Cited
OTHER PUBLICATIONS

Ruzicka, "Helv. Chim. Acta.", vol. 4, pp. 472–482 (1921).
Marvel et al., "J. Org. Chem.", vol. 22, pp. 1065–1067 (1957).
Moriarty et al., "J. Org. Chem.", vol. 29, pp. 2748–2750 (1964).
Ciaperoni et al., Chim. Ind. (Milan), vol. 50, pp. 772–773 (1968).
Novikov et al., IZV. Vyssh. Vohed. Zazed., Khim. Khim. Tekhnol. (1973), vol. 16, No. 2, pp. 304–305. Abstracted in *Chemical Abstracts*, vol. 78 (1973), Item 159395.

*Primary Examiner*—Natalie Trousof
*Assistant Examiner*—Robert T. Bond
*Attorney, Agent, or Firm*—Burgess Ryan and Wayne

[57] ABSTRACT

A process for preparing pure N-alkyl-lactams obtained by the reaction, in an organic solvent medium of, the corresponding lactamate of an alkali metal and an alkyl halide. This process consists of treating a reactive mixture of N-alkyl-lactam containing the corresponding cyclo-alkylene imine as an impurity with a current of carbon dioxide, until the cyclo-alkylene imine precipitates completely in the form of an insoluble carbonate, and then separating it from the precipitate.

10 Claims, No Drawings

PROCESS FOR PREPARING N-ALKYL-LACTAMS

This invention concerns a process for preparing pure N-alkyl-lactams of the general formula:

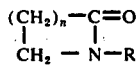

where R is a saturated aliphatic hydrocarbon radical, the linear or branched chain of which comprises 6 to 20 carbon atoms, and $n$ is an integer between 4 and 14.

It is known that homopolymers can be obtained from N-alkyl-lactams. But the resulting products are of a liquid or paste-like consistency, with low molecular weights. When copolymerized with lactams such as caprolactam, decalactam, undecanolactam, and dodecalactam, and in a proportion of less than 50%, N-alkyl-lactams provide copolyamides having mechanical properties different from those of lactam-derived polyamides, and exhibiting more particularly a greater flexibility.

German Patent specification No. 859,016 describes a process for preparing certain N-alkyl-lactams such as N-alkylcaprolactams or N-alkyl-pyrollidones, in which an alkyl halide is reacted with an alkali lactamate obtained by the reaction of an alkali metal and the lactam in an inert solvent.

Alkyl-lactams prepared in this way contain, after separation by distillation, a significant proportion of the cyclo-alkylene imine corresponding to the lactam used, and which forms during the reaction between the lactam and the metal, by reduction of the carbonyl group of the lactam. The presence of cyclo-alkylene imine as an impurity in the synthetized N-alkyl-lactam makes it impossible or extremely difficult to copolymerize lactam with an N-alkyl-lactam, so that any substances thus produced are useless.

The instant invention overcomes these drawbacks by providing a process that produces extremely pure N-alkyl-lactams, more specifically N-alkyldodecalactams.

In this novel process, the N-alkyl-lactam solution, obtained by a reaction between the alkali lactamate and an alkyl halide in an inert solvent containing as an impurity the alkylene imine corresponding to the lactam used, is treated at atmospheric temperature with a current of carbon dioxide, until the alkylene imine precipitates completely, and is then separated from the precipitate. Fractionated distillation of the resulting solution produces an extremely pure N-alkyl-lactam, suitable for any type of copolymerization with at least one other lactam or amino-acid or diamine and diacid salt.

The flow of carbon dioxide precipitates the cycloalkylene imine in the reactive mixture, is in the form of an insoluble carbonate.

The operation is performed by bubbling the carbon dioxide through the solution, for a period of 10 to 60 minutes, depending on the flow-rate and the dispersal of the gas in the reactive mixture; said period is usually between 15 and 20 minutes. Bubbling is stopped when part of the filtered solution remains limpid under the effect of the carbon dioxide.

The insolubilized alkylene imine can then be eliminated from the reaction solution by any conventional process for separating solid and liquid phases, such as filtration, decanting or centrifugation.

The solvent is then evaporated from the resulting solution, and fractionated distillation performed under high vacuum, producing extremely pure N-alkyl-lactam.

The alkali lactamate is obtained by reaction in an inert solvent between a lactam and an alkali metal such as sodium, potassium, lithium or their hydrides, used in the form of a fine powder.

The alkali lactamate can also be prepared by the reaction, in an inert solvent, between the lactam and alkali alcoholates, such as sodium methylate or alkaline metal alkyls, such as butyl-lithium. Suitable alkyl halides include alkyl chlorides, bromides and iodides, in which the halogen atom is attached to the end of the hydrocarbon chain, such as 1-bromoheptane, 1-bromononane, 1-bromodecane, 1-bromododecane, 1-bromocetone, 1-chloro-undecane, and 1-bromo-2-ethylhexane.

Bromides are particularly suitable for this reaction, and can be prepared with great efficiency by the reaction of hydrobromic acid with the corresponding alcohol. The inert solvent is suitably selected from the group comprising saturated armoatic, aliphatic or cyclo-aliphatic hydrocarbons, and aliphatic, cyclo-aliphatic or aromatic ethers, such as benzene, toluene, xylene, ethylbenzene, octane, decane, cyclehexane, cyclododecane, butyl oxide and tetrahydrofuran.

The inert solvent within which the reaction between alkali lactamate and alkyl halide takes place may be used as a solvent in the subsequent operations to separate and purify the N-alkyl-lactam, particularly as regards elimination of the alkylene imine, through the action of carbon dioxide on the reactive medium formed by the reaction products dissolved in the inert solvent, after successive elimination by hot filtration of the alkali halide formed in the reaction and by crystallization in the cold state or part of the lactam that has failed to react.

The following examples will illustrate the invention, which is, however, in no way confined to them.

EXAMPLE 1

98.7 g (0.5 mol) of pure dodecalactam and 400 ml of xylene were placed in a one-litre reactor fitted with a stirring device, thermometer and reflux cooler. This mixture was heated to 80°C while being stirred, and when the lactam was dissolved, 19.2 g metallic sodium was introduced in small amounts. Hydrogen was set free and the temperature rose quickly. The temperature was maintained until the metallic sodium had completely disappeared. As soon as the organic solution was limpid, 72 g (0.4 mol) 1-bromoheptane was added, while the temperature was kept at 130°C, and stirring continued for two hours after the 1-bromoheptane had been added. The mixture was then cooled to 70°C, and the sodium bromide that had formed in the reaction was filtered at this temperature, and washed with a small quantity of xylene, which was then added to the reactive solution. The mixture was then cooled to atmospheric temperature, whereupon approximately 15 g of dodecalactam that had not reacted precipitated. This was filtered and washed with xylene, which was then added to the reactive solution. The solution was then treated at ordinary temperature with a flow of carbon dioxide, which caused the cyclo-dodecamethylene imine to be precipitated, whereafter the precipitate was removed by filtration. The xylene was recovered from the filtrate by evaporation at reduced pressure.

The reactive product obtained after elimination of the xylene was distilled in a high vacuum (2 mm Hg) thus producing two fractions and a residue of 5 g. The first fraction, consisting of the distillate obtained at a temperature of not less than 180°C, and weighing 20.5 g, consisted mainly of dodecalactam. The second fraction, boiling point 180° to 183°C, weighing 86.5 g, was almost pure N-heptyl dodecalactam $n_D^{24} = 1.483$ $d_4^{26} = 0.947$.

The infrared spectra of these products showed the same characteristic >CO and —NH— absorption bands as those appearing in the N-heptyldodecalactam spectrum.

TABLE 1

| Example number | 2 | 3 | 4 | 5 |
|---|---|---|---|---|
| Product | N-nonyl dodecalactam | N-decyl dodecalactam | N-dodecyl dodecalactam | N(2-ethyl-hexyl) dodecalactam |
| Boiling point | $Eb_{2m}=194°C$ | $Eb_{1.5mn}=198°$ | $Eb_{0.5mn}=210°C$ | $Eb_{1.7mn}=184°C$ |
| Density $d_4^{25}$ | 0.920 | 0.915 | 0.873 | 0.919 |
| Refractive index | 1.480 | 1.482 | 1.482 | 1.484 |
| Elementary analysis | | | | |
| Molecular weight | | | | |
| found | 323.57 | 337.59 | 365.65 | 309.54 |
| calculated | 323.33 | 337.56 | 365.62 | 309.55 |
| Carbon | | | | |
| found | 77.82 | 78.00 | 72.80 | 78.82 |
| calculated | 77.95 | 78.27 | 78.84 | 77.61 |
| Hydrogen | | | | |
| found | 12.80 | 12.98 | 13.01 | 12.74 |
| calculated | 12.77 | 12.94 | 12.96 | 12.70 |
| Nitrogen | | | | |
| found | 4.36 | 4.30 | 3.80 | 4.57 |
| calculated | 4.33 | 4.15 | 3.83 | 4.53 |

| | Experimental result | Calculated result |
|---|---|---|
| Molecular weight | 285.5 | 285 |
| Carbon | 77.0 | 77.2 |
| Hydrogen | 12.5 | 12.6 |
| Infrared spectrum | >C = 0 | 1650 cm$^{-1}$ |
| | —NH— | 3310 cm$^{-1}$ |
| Nitrogen | 4.82 | 4.74 |

The selectivity in N-heptyl dodecalactam (0.293 mol) with respect to dodecalactam consumption (0.325 mol) was 90%.

EXAMPLES 2 TO 5

Using the same process as in example 1, N-nonyldodecalactam, N-decyldodecalactam, N-dodecyldodecalactam and N(2-ethyl-hexyl)dodecalactam were obtained with levels of selectivity of between 75 and 90% of dodecalactam consumption.

The results of the analysis of the resulting products are shown in table 1.

EXAMPLE 6

This example is given to show the effect of plasticization or improved flexibility of a polyamide resulting from copolymerization of dodecalactam with N-heptyldodecalactam, as compared to the 12-polyamide resulting from dodecalactam homopolymerization.

60.3 g (0.25 mol) N-heptyldodecalactam, 118.98 g (0.75 mol) dodecalactam, 0.3586 orthophosphoric acid and 13.5 water were placed in a ½ litre autoclave equipped with a stirring system.

The apparatus was scavenged with an inert gas, such as nitrogen or argon, and then filled with pressurized inert gas. The temperature was raised during two hours to 300°C, and pressure was raised to 20 bars. This temperature and pressure were maintained for 4 hours, while mechanical stirring was continued. The apparatus was then cooled to 260°C, and gradually depressurized from 20 bars to atmospheric pressure. The apparatus was kept at 260°C, and stirring continued for 5 hours, while inert gas was blown through the autoclave at atmospheric pressure without interruption. The operation was terminated by heating and stirring for 6 hours in a 1 mm Hg vacuum.

The resulting polymer was white, transparent in a thin layer, and had an inherent viscosity of 1.35 at 25°C, with a concentration of 0.5% in metacresol. It had the following physical and mechanical properties, compared with a 12-polyamide produced from dodecalactams:

TABLE 2

| | N-heptyldodecalactam and dodecalactam copolymer | 12-polyamide produced from dodecalactam |
|---|---|---|
| Melting point | 150°C | 175°C |
| Vitreous transition point | −25°C | 50°C |
| Tensile strength; velocity 14 mm/mm at 20°C 65% relative humidity | | |
| elastic limit | 20% | 16% |
| Stress | 125 bars | 360 bars |
| Elongation at rupture | 220% | 200% |
| Stress | 270 bars | 450 bars |
| Dynstat impact | unbroken | unbroken |
| G-torsion modulus of rigidity | (1.10$^3$ kg/cm$^2$ at 0°C (2.5.10$^3$ kg/cm$^2$ | (5.10$^3$ kg/cm$^2$ at 0°C (5,5.10$^3$ kg/cm$^2$ |

TABLE 2-continued

| | N-heptyldodecalactam and dodecalactam copolymer | 12-polyamide produced from dodecalactam |
|---|---|---|
| (ASTM standard D 1043) | at −20°C | at −20°C |

What is claimed is:

1. A process for preparing pure N-alkyl-lactams obtained by the reaction of the corresponding lactamate of an alkali metal and an alkyl halide and having the general formula:

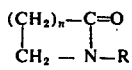

where R is a saturated hydrocarbon aliphatic radical, the linear or branched chain of which comprises between 6 and 2 carbon atoms, and $n$ is an integer between 4 and 14, which comprises reacting the N-alkyl-lactam in an organic solvent, containing the corresponding cycloalkylene imine as an impurity, at atmospheric temperature with a flow of carbon dioxide until the cycloalkylene imine precipitates completely in the form of an insoluble carbonate, and is then separated from the precipitate.

2. The process of claim 1, for preparing pure N-heptyldodecalactam, wherein an organic solution of N-heptyldodecalactam is treated at atmospheric temperature with a flow of carbon dioxide, until the cyclododecamethylene imine precipitates completely in the form of an insoluble carbonate, and is then separated from the precipitate.

3. The process of claim 1, for preparing pure N-nonyldodecalactam, wherein an organic solution of N-nonyldodecalactam is treated at atmospheric temperature with a flow of carbon dioxide, until the cyclododecamethylene imine precipitates completely in the form of an insoluble carbonate, and is then separated from the precipitate.

4. The process of claim 1, for preparing pure N-decyldodecalactam, wherein an organic solution of N-decyldodecalactam is treated at atmospheric temperature with a flow of carbon dioxide, until the cyclododecamethylene imine precipitates completely in the form of an insoluble carbonate, and is then separated from the precipitate.

5. The process of claim 1, for preparing pure N-dodecyldodecalactam, wherein an organic solution of N-dodecyldodecalactam is treated at atmospheric temperature with a flow of carbon dioxide, until the cyclododecamethylene imine precipitates completely in the form of an insoluble carbonate, and is then separated from the precipitate.

6. The process of claim 1, for preparing pure N(2-ethyl-hexyl)dodecalactam, wherein an organic solution of N(2-ethyl-hexyl)dodecalactam is treated at atmospheric temperature with a flow of carbon dioxide, until the cyclododecamethylene imine precipitates completely in the form of an insoluble carbonate, and is then separated from the precipitate.

7. A process according to claim 1, wherein said carbon dioxide is allowed to bubble through said N-alkyl lactam solution for a period of about ten to sixty minutes.

8. A process according to claim 7, wherein said carbon dioxide is bubbled through said solution for a period of fifteen to twenty minutes.

9. A process according to claim 1, wherein said organic solvent is a member selected from the group consisting of a saturated aromatic, aliphatic or cycloaliphatic hydrocarbon, an aliphatic, cycloaliphatic and aromatic ether.

10. A process according to claim 9, wherein said aromatic, aliphatic or cycloaliphatic hydrocarbon is a member selected from the group consisting of benzene, toluene, xylene, ethyl benzene, octane, decane, cyclohexane, butyl oxide and tetrahydrofuran.

* * * * *